United States Patent [19]

Salibello et al.

[11] Patent Number: 4,998,820

[45] Date of Patent: Mar. 12, 1991

[54] INSTRUMENT AND METHOD FOR USE IN OPTOMETRIC EXAMINATIONS

[75] Inventors: Cosmo Salibello; Jonathan G. Torrey; Steven G. Coffman; Gerald M. Murch, all of Portland, Oreg.

[73] Assignee: Applied Vision Concepts, Inc., Portland, Oreg.

[21] Appl. No.: 282,596

[22] Filed: Dec. 12, 1988

[51] Int. Cl.$^5$ ............................................. A61B 3/02
[52] U.S. Cl. .................... 351/243; 351/203; 351/239
[58] Field of Search ............... 351/203, 233, 239, 240, 351/243

[56] References Cited

U.S. PATENT DOCUMENTS

| Re. 28,921 | 8/1976 | Haines et al. | 351/23 |
|---|---|---|---|
| 4,239,351 | 12/1980 | Williams et al. | 351/36 |
| 4,285,580 | 8/1981 | Murr | 351/35 |
| 4,412,729 | 11/1983 | Hartmann | 351/239 |
| 4,511,228 | 4/1985 | von Gierke et al. | 351/243 |
| 4,564,274 | 1/1986 | Clark | 351/233 |
| 4,576,454 | 3/1986 | Charney et al. | 351/243 |
| 4,611,893 | 9/1986 | Schrier | 351/239 |
| 4,764,007 | 8/1988 | Task | 351/243 |

*Primary Examiner*—Paul M. Dzierzynski
*Attorney, Agent, or Firm*—Dellett, Smith-Hill and Bedell

[57] ABSTRACT

An optical instrument for use in conducting optometric examinations which generates an alphanumeric type display simulating the optical features of displays provided by video display terminals. The instrument comprises a light source and a multi-layered screen through which light from the source may be transmitted. The screen employs light from the source in forming characters which are comprised of pixel-like light elements similar to those making up VDT generated characters. Further, the screen is operative for degrading the image quality of the characters by transforming the light elements into Gaussian type spatial profiles typical of the pixels generated by VDTs.

3 Claims, 1 Drawing Sheet

INSTRUMENT AND METHOD FOR USE IN OPTOMETRIC EXAMINATIONS

BACKGROUND OF THE INVENTION

The present invention relates to vision testing equipment and more specifically to instruments and methods for use in conducting optometric examinations.

As the use of video display terminals has become more widespread, so too have certain ophthalmological afflictions associated with their utilization. The alphanumeric characters displayed on video screens are made up of dots or pixels which do not have well defined borders and therefore are difficult for the eye to focus upon. Further, since video screens are maintained at a constant distance of about 50 cm from the user's eyes, the same eye muscles are in constant use in focusing on the screens. These factors cause significant amounts of stress and fatigue on the eyes of video display terminal users which is often aggravated by the fact that many such users utilize their equipment for extended periods on a day after day basis. The stress associated with video display use frequently results in peculiar types of eye problems requiring special corrective prescriptions in the spectacles selected for the users afflicted with these problems.

In order to accurately diagnose these problems, appropriate test equipment and test procedures must be provided. In accordance with the process currently used by medical practitioners to determine the spectacle requirements of typical patients, an apparatus is placed in front of the eyes of the patient which enables the doctor to rapidly change a wide selection of lenses while the patient views a set of test images through the lens changing apparatus. As the patient focuses on the test images, the doctor assesses the status of the muscles inside the patients eyes and judges their degree of relaxation through the use of a retinoscope. The doctor determines the combination of lenses and the prescription best suited to the patient by changing the lenses until he detects the combination which provides the most relaxed state in the eye muscles of the patient.

As may be understood from the above, the fitting of corrective lenses is basically a trial and error process in which the doctor observes the reaction of the patient's eye muscles to an appropriate test image for different combinations of lenses. However, without a test image which accurately simulates the conditions under which the patient may experience eye problems, a prescription for suitable corrective lenses may not be reliably determined.

Currently available equipment does not provide a satisfactory system for generating test images which simulate the characteristics of video display terminals. Consequently, most medical practitioners have been left with no recourse except to make educated guesses as to the lens corrections which may work best for their patients and to have their patients go back to work and try the new prescription out. This is, however, a time consuming, expensive, inaccurate and generally unsatisfactory method of proceeding to provide spectacle prescriptions.

It is therefore an object of the present invention to provide an improved system for testing the vision of video display terminal users which allows for accurate determination of the best corrective lens prescriptions for such patients.

It is another object of the present invention to provide an improved apparatus which accurately simulates alphanumeric characters as presented on a video display screen and which can be conveniently used in accordance with current optometric test procedures.

It is a further object of the present invention to provide an improved optometric instrument for use in determining prescriptions for corrective lenses which is economical, compact and simple to use.

SUMMARY OF THE INVENTION

The present invention comprises an optical instrument for use in optometric examinations which simulates the optical features of alphanumeric displays provided by video display terminals. The instrument comprises a light source such as a group of incandescent bulbs and a multi-layered screen through which light from the source may be directed to a patient viewing the screen. The screen comprises a printed layer including sets of small openings or pixels which cooperatively define alphanumeric characters in terms of multiple pixel-like elements of light from the light source. The screen further comprises a mechanism for degrading the alphanumeric character images by reducing the higher spatial frequencies of light associated with the light elements which define the characters.

In the preferred embodiment, the screen includes a lensing structure made of layers of plastic sheet materials having different indexes of refraction which refract the light from the light elements and provide said light elements with Gaussian profiles typical of the pixels formed by video display terminals in defining display characters. The preferred embodiment also includes a layer of diffusing material located adjacent the light source, functional in uniformly dispersing light from this light source. In operation, the light elements and lensing structure work together to generate an alphanumeric character display which accurately simulates the characteristics of the displays provided by video display terminals.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

DESCRIPTION OF THE PREFERRED EMBODIMENT

Figure 1:
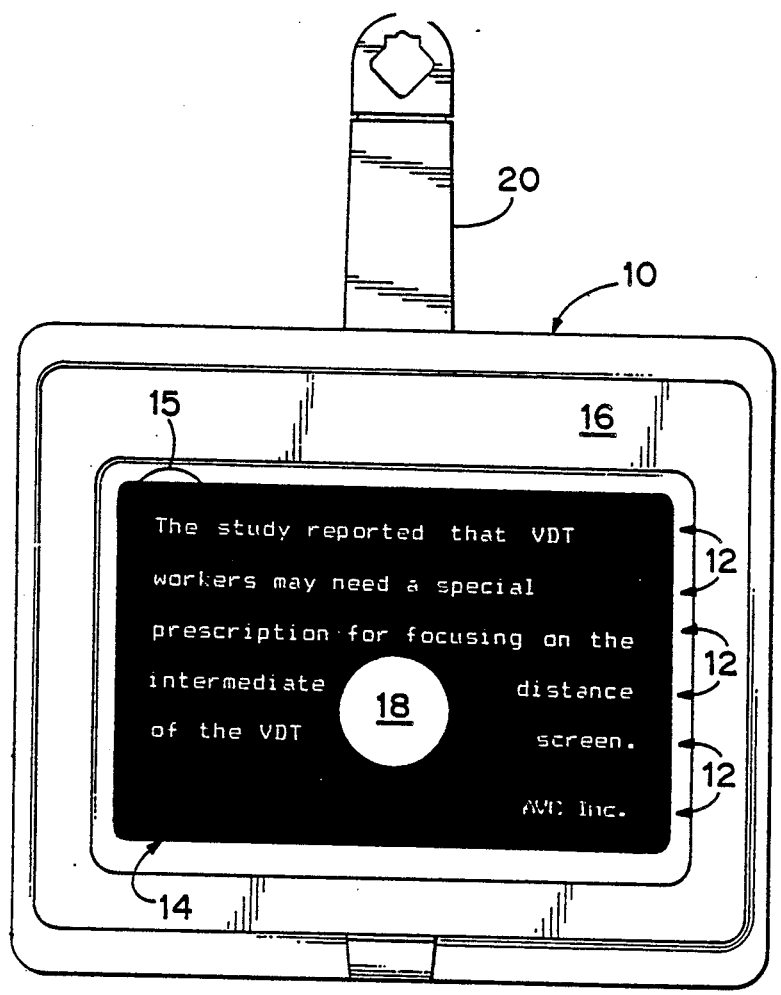
FIG. 1 is a front view of an apparatus corresponding to one embodiment of the present invention showing a display of alphanumeric characters in accordance with the invention.
Figure 2:
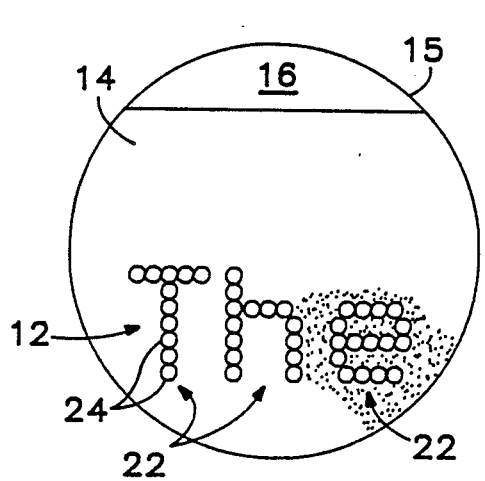
FIG. 2 is an enlarged view of a group of alphanumeric characters from FIG. 1 illustrating the details of the construction of the characters which make up the display shown in FIG. 1.

Referring now to FIG. 1, the apparatus 10 for simulating a video display terminal ("VDT") constitutes one embodiment of the present invention in which six lines 12 of alphanumeric characters are provided for viewing by a patient during an optometric examination. The lines 12 are presented on a multi-layered screen 14 which is mounted in the frame 16. A viewing tunnel 18 allows the medical practitioner conducting the optometric exam to directly view the patient's eyes from behind the apparatus 10 during the course of the examination, while support arm 20 allows the apparatus 10 to be conveniently mounted and readily swung into position for use when desired. As shown by FIG. 2 which provides a close-up view of the region within circle 15 in FIG. 1, alphanumeric characters 22 are made up of sets of pixel-like elements 24 disposed in 7×9 matrices in a manner similar to the characters displayed on many video display terminals.

Figure 3:
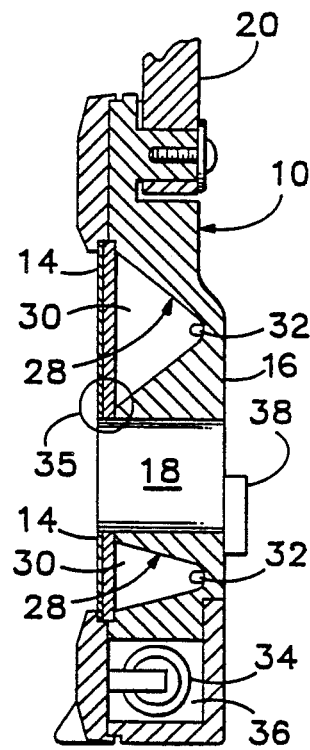
FIG. 3 is a cross sectional side view of the apparatus shown in FIG. 1 illustrating the operative components associated with the present invention.

Referring now to FIG. 3, the VDT simulation apparatus 10 includes a cavity 30 which extends around the viewing tunnel 18 in a rectangular pattern. The cavity 30 is parabolically-shaped outwardly from the viewing tunnel 18, with a number of incandescent bulbs 32 being positioned within the cavity 30 at focus locations defined by the parabolic shape of the cavity 30. The bulbs 32 and the cavity 30 operate as a light source 28 which provides light directed forwardly through the screen 14. A battery 34 is mounted within a small chamber 36 and is connected to the bulbs 32 through the switch 38 and functions as the power source for the bulbs 32 such that illumination is provided to the screen 14 when the switch 38 is turned on.

Figure 4:
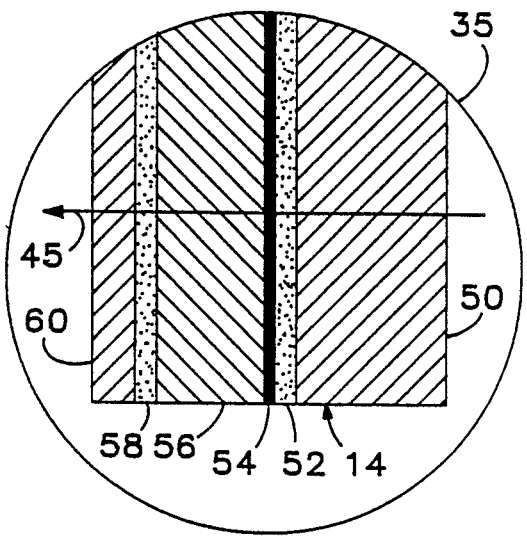
FIG. 4 is an enlarged cross sectional view of the multi-layered screen component of FIG. 3 illustrating the construction of the screen which is central to the functionality of the present invention.

Referring now to FIG. 4, providing a close-up view of the region within circle 35 in FIG. 3 screen 14 is comprised of a number of adjacent layers or sheets of material through which light from the source 28 as represented by the light ray 45 must pass in order to be emitted from the apparatus 10. In the preferred embodiment, the screen 14 includes six separate layers 50, 52, 54, 56, 58 and 60. Layer 50 comprises a 0.125 inch thick sheet of acrylic plastic having a "milky" appearance which acts to diffuse the light from the bulbs 32 and thereby assure more uniform illumination of the screen 14 while avoiding hot spots corresponding to the bulb positions. The layer 54 is comprised of a very thin film or mask of vinyl ink printed onto the back of layer 56. The layer 54 is applied via silk screen printing techniques in a pattern which is made up of sets of small circular openings or pixels which cooperatively define the alphanumeric characters 22. The layer 56 comprises a 0.020 inch thick sheet of polycarbonate plastic having a color which is appreciated by the normal human eye as a mid-saturation green hue. The coloration of the layer 56 affects the light transmitted through the screen 14 and results in the transmitted light approaching the color of the light generated by excitation of the P31 phosphor commonly used in VDTs. The components of the screen 14 thus far described are bonded together by the layers 52 and 58 which may comprise a series of relatively narrow and widely spaced-apart strips of acrylic adhesive which physically separate or space the other layers of the screen 14 while joining them together. It should be noted that the layers 52 and 58 largely comprise air spacings and have a substantially lower index of refraction than the layer 56, which leads to certain desirable optical effects hereinafter described. The final exterior layer 60 of the screen 14 comprises a 0.010 inch sheet of polycarbonate plastic functioning as a cover and providing an anti-glare surface for the screen 14. The layer 60 is also selected to be of sufficient thickness to function in combination with other layers 50, 52, 56 and 58 to attenuate the light forming the characters 22 to the extent required to provide approximately a 3 to 1 contrast ratio between the characters and their surrounding background in a manner similar to the contrast found in VDTs.

In operation, the design of the screen 14 provides optically unique characteristics on two levels. First, the pixels incorporated into the printed layer 54 allow the characters 22 to be formed from corresponding elements of light as transmitted through the screen 14. The characters 22 are thereby constructed of pixel-like elements of light in a manner analogous to characters displayed on VDTs. Second, since the layers 52 and 58 provide a lower index of refraction than the layers 54, the arrangement of these particular layers forms a lensing structure which operates to refract the light of the elements forming the characters 22 and reduce the higher order spatial frequencies associated with the light elements. The light elements forming the characters 22 are effectively defocussed and the borders of the characters 22 are thereby "blurred" degrading the quality of image provided by the apparatus 10. The layers 52, 56 and 58 are selected to provide amounts of refraction sufficient to transform the spatial distribution of the light comprising the individual pixel elements into Gaussian type profiles when viewed from a distance of approximately 50 cm from the screen 14. The Gaussian profiles of the light elements provided are very similar to the Gaussian type profiles characteristic of the pixels generated by VDTs for use in forming characters. The characters generated by VDTs are simulated in two important respects through the use of pixel-like light elements and by providing elements having an appropriately degraded image quality, the latter effect being achieved through a non-complex layer construction.

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. An optical system for use in conducting optometric examinations on patients who suffer from eye fatigue due to the use of VDT displays, said system comprising:
   (a) a light source including a parabolic shaped cavity having a viewing means extending therethrough for allowing a medical practitioner conducting an optometric exam to view the patient's eyes during the exam, and a plurality of light emitting means, said light emitting means being disposed in said cavity at a plurality of focus locations of said cavity;
   (b) a plurality of pixel means for defining alphanumeric characters in terms of pixel-like light elements in a manner similar to a VDT using light from said source; and
   (c) means for modifying the spatial light distribution profile of the light elements defining said alphanumeric characteristics in order to simulate the characteristics of pixels presented on a VDT display.

2. An optical system for use in conducting optometric examinations on patients who suffer from eye fatigue due to the use of VDT displays, said system comprising:
(a) a light source;
(b) a plurality of pixel means for defining alphanumeric characters in terms of pixel-like light elements in a manner similar to a VDT using light from said source, wherein said pixel-like elements are provided in a layer having small circular light-transmitting openings; and
(c) means for modifying the spatial light distribution profile of the light elements defining said alphanumeric characters in order to simulate the characteristics of pixels presented on a VDT display.

3. An optical display method for use in conducting optometric examinations by providing a plurality of alphanumeric characters formed from sets of light elements characterized by approximately Gaussian light amplitude curves comprising the steps of:
transmitting light from a light source through a screen having sets of openings which function to cooperatively define said alphanumeric characters in terms of pixel-like light elements, said step of transmitting light from a light source further including the step of disposing said light source in at least one focus location of a parabolic shaped cavity; and
degrading the quality of the images provided by said light elements by selectively reducing the higher order spatial frequencies associated with the light transmitted through said openings.

* * * * *

UNITED STATES PATENT AND TRADEMARK OFFICE
CERTIFICATE OF CORRECTION

PATENT NO. : 4,998,820

DATED : March 12, 1991

INVENTOR(S) : COSMO SALIBELLO, et al

It is certified that error appears in the above-identified patent and that said Letters Patent is hereby corrected as shown below:

Column 5, line 1, "characteristics" should be --characters--.

Signed and Sealed this

Twenty-eighth Day of July, 1992

Attest:

DOUGLAS B. COMER

*Attesting Officer*   *Acting Commissioner of Patents and Trademarks*